(12) United States Patent
Harnisch et al.

(10) Patent No.: US 10,767,150 B2
(45) Date of Patent: Sep. 8, 2020

(54) EXPANSION KIT FOR BIOREACTORS USED FOR PERFORMING MICROBIAL BIO-ELECTROSYNTHESIS

(71) Applicant: HELMHOLTZ-ZENTRUM FUR UMWELTFORSCHUNG GMBH—UFZ, Leipzig (DE)

(72) Inventors: Falk Harnisch, Leipzig (DE); Steffi Hunger, Leipzig (DE); Andreas Zehnsdorf, Leipzig (DE); Daniel Beyer, Leipzig (DE); Luis Felipe Morgado Rosa, Leipzig (DE)

(73) Assignee: HELMHOLTZ-ZENTRUM FUR UMWELTFORSCHUNG GMBH—UFZ, Leipzig (DE)

( * ) Notice: Subject to any disclaimer, the term of this patent is extended or adjusted under 35 U.S.C. 154(b) by 285 days.

(21) Appl. No.: 15/100,961

(22) PCT Filed: Dec. 2, 2014

(86) PCT No.: PCT/EP2014/076293
§ 371 (c)(1),
(2) Date: Jun. 1, 2016

(87) PCT Pub. No.: WO2015/082490
PCT Pub. Date: Jun. 11, 2015

(65) Prior Publication Data
US 2016/0312167 A1   Oct. 27, 2016

(30) Foreign Application Priority Data
Dec. 2, 2013 (DE) .................... 10 2013 224 673

(51) Int. Cl.
*C12M 1/00* (2006.01)
*C12M 1/12* (2006.01)
(Continued)

(52) U.S. Cl.
CPC ............ *C12M 23/42* (2013.01); *C12M 23/02* (2013.01); *C12M 23/08* (2013.01); *C12M 23/20* (2013.01);
(Continued)

(58) Field of Classification Search
CPC .............................. C12M 23/42; C12M 23/34
(Continued)

(56) References Cited

U.S. PATENT DOCUMENTS 4,296,205 A   10/1981   Verma
4,772,558 A    9/1988   Hammann
(Continued)

FOREIGN PATENT DOCUMENTS

DE   2018289 A1   3/1972
DE   3703608 A1   8/1987
(Continued)

OTHER PUBLICATIONS

Machine translation of Document No. JP 2012085600 A provided by Japan Platform for Patent Information, Matsumoto, 2012 (Year: 2012).*
(Continued)

*Primary Examiner* — Holly Kipouros
(74) *Attorney, Agent, or Firm* — Perkins Coie LLP; Jordan Becker

(57) ABSTRACT

The aim of the invention is to design an expansion kit (100) for bioreactors (20) which allows prior art bioreactors (20) to be expanded in a way that makes the same usable for microbial bio-electrosynthesis. In order to achieve said aim, the expansion kit (100) comprises a reaction chamber (21) which is open on one side and which has a window (23) in a sidewall (22), said window (23) being provided with a membrane (24).

6 Claims, 2 Drawing Sheets

Figure 1:
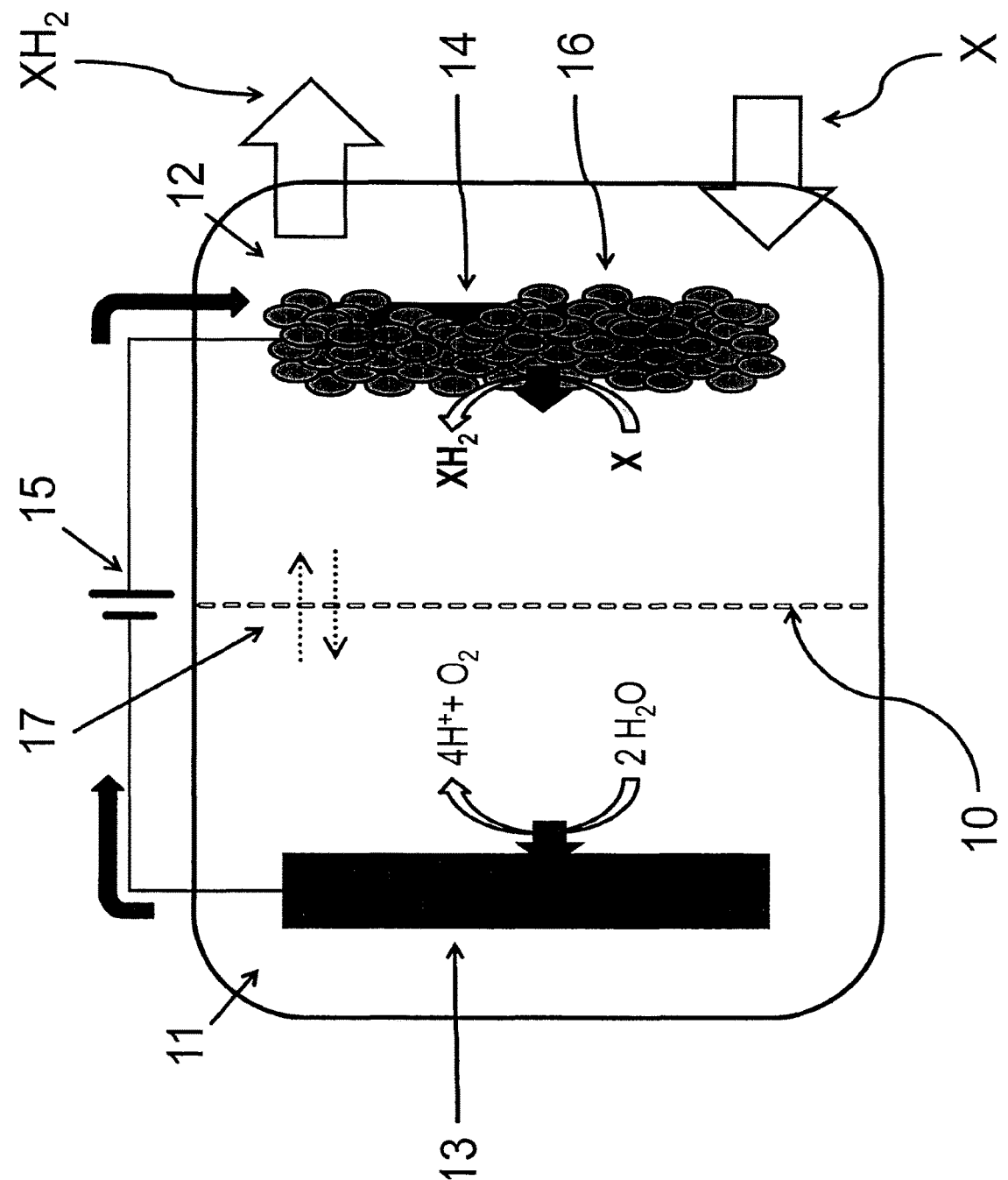

(51) Int. Cl.
*C12N 13/00* (2006.01)
*C12M 3/00* (2006.01)
*C12M 1/24* (2006.01)
*C12M 1/26* (2006.01)

(52) U.S. Cl.
CPC ............ *C12M 23/28* (2013.01); *C12M 23/34* (2013.01); *C12M 23/44* (2013.01); *C12M 25/02* (2013.01); *C12M 33/14* (2013.01)

(58) Field of Classification Search
USPC ....................................................... 435/289.1
See application file for complete search history.

(56) References Cited

U.S. PATENT DOCUMENTS

| | | | | |
|---|---|---|---|---|
| 5,624,544 | A | * | 4/1997 | Deguchi ............... C02F 1/4618 204/253 |
| 2009/0221068 | A1 | | 9/2009 | Kobayashi et al. |
| 2011/0315562 | A1 | * | 12/2011 | Basseyguy ................ C25B 1/04 205/638 |
| 2013/0062196 | A1 | * | 3/2013 | Sin ........................ C02F 1/4618 204/228.6 |
| 2013/0256149 | A1 | | 10/2013 | Popat et al. |

FOREIGN PATENT DOCUMENTS

| | | | | |
|---|---|---|---|---|
| DE | 69209077 | A1 | | 8/1992 |
| DE | 10350972 | A1 | | 8/2005 |
| DE | 102011054364 | A1 | | 4/2013 |
| EP | 0170098 | A2 | | 2/1986 |
| EP | 2151491 | A2 | | 2/2010 |
| EP | 2653531 | A1 | | 10/2013 |
| FR | 2085387 | A1 | | 12/1971 |
| GB | 2297926 | A | | 8/1996 |
| JP | 2011188830 | A | * 9/2011 | ............ C12M 23/38 |
| JP | 2012085600 | | * 5/2012 | |
| WO | 89/05167 | A1 | | 6/1989 |
| WO | 2000003447 | A1 | | 1/2000 |
| WO | 2005003284 | A2 | | 1/2005 |
| WO | 2007037407 | A1 | | 4/2007 |
| WO | 2009087448 | A2 | | 7/2009 |
| WO | 2010117864 | A1 | | 10/2010 |
| WO | 2011062485 | A2 | | 5/2011 |
| WO | 2013120853 | A1 | | 8/2013 |

OTHER PUBLICATIONS

Machine translation of document entitled JP 2011188830 provided by Espacenet, Kudo et al., 2011 (Year: 2011).*
European Patent Office, International Search Report for PCT/EP2014/076293, dated Feb. 13, 2015, 4 pgs.

* cited by examiner

EXPANSION KIT FOR BIOREACTORS USED FOR PERFORMING MICROBIAL BIO-ELECTROSYNTHESIS

This invention relates to an expansion kit for bioreactors used for performing microbial bio-electrosynthesis, a bioreactor and the use thereof.

Microbial bio-electrosynthesis or microbial electrochemical technology is currently experiencing a considerable boom globally. The aim of microbial bio-electrosynthesis is to link microbial synthesis, preferably by means of extracellular electron transfer, to the flow of electrical current. Electrical current can thereby be implemented both during oxidation processes on anodes and during reductions on the cathode. In both cases, the microbial chemical change is associated with the flow of electrical current.

In this case, microbial bio-electrosynthesis has numerous advantages such as potentially higher selectivities, yields, etc. compared with traditional electrochemical synthesis, but it also offers advantages compared with enzymatic bio-electrosyntheses since, in most cases, only a maximum of 2 electrons can be transferred per stage of the reaction and the catalyst is not self-regenerating.

The term "microbial bio-electrosynthesis" can include three fundamental classes of processes, including:
i) synthesis of $CO_2$,
ii) "refinement" of precursors, and
iii) electrochemical fermentation control.

The range of products, in this case, is potentially very diverse.

Research in this field, in particular in process engineering terms, is at the initial stage with respect to the technology used and is predominantly being carried out in laboratory experiments of a small size of, for example, 100 mL and in "self-assembly reactors" with a size of mostly <1 L, wherein no or only minor process monitoring and control are carried out.

Since, however, global interest in microbial bio-electrosynthesis is simultaneously increasing, it must be assumed that the need for suitable bioreactor technology, which allows comparable results, will increase. For this reason, the need for comparable laboratory reactor systems for performing microbial electrosynthesis experiments will also increase.

The term "membrane reactor" is very broadly defined in technical usage. The term is therefore used to denote, for example, reactors with ceramic membrane tubes, in order to cause various substances to react chemically with one another, as well as the plurality of reactors with membranes for retaining microorganisms in wastewater treatment. These are not suitable for performing microbial bio-electrosynthesis.

Reactors which are suitable for performing microbial bio-electrosynthesis are disclosed, for example, in the printed publications US 2013/0256149 A1, WO 2011/062485 A2, WO 2010/117864 A1 and WO 00/03447, wherein these systems are "stand-alone" systems which are not suitable for integration into existing/available bioreactor systems, so that these cannot be directly connected to the analytics available in existing infrastructures and cannot exploit the available expertise or scaling.

The object of the invention is to therefore design an expansion kit for bioreactors which allows prior art bioreactors to be expanded in a way that makes the same usable for microbial bio-electrosynthesis.

This object is achieved by an expansion kit for bioreactors having the features of Claim 1.

To this end, the invention proposes to design an expansion kit for bioreactors used for performing microbial bio-electrosynthesis, which comprises a reaction chamber which is open on one side, preferably the upper side, and which has a preferably rectangular window and/or a corresponding through-opening in a sidewall, said window being provided with a preferably reversibly fixed membrane.

The membrane is an ion-selective membrane, for example a Nafion membrane or a ceramic membrane. Suitable membranes are in principle known to the person skilled in the art.

According to a preferred embodiment, the reaction chamber comprises a cross-section in the form of a circular segment, wherein the window is configured in the area of the chord.

The side surface produced by the chord can also be constituted differently, so that a rounded or angular indentation having a window at the lowest point can also be located in the wall of the reaction chamber. It is crucial that due to the configuration of the reaction chamber a second reaction chamber is created in the bioreactor which is to be retrofitted, which usually has a circular cross-section. In this case, the configuration of a planar sidewall for receiving the window and/or the through-opening is preferred.

Reactors are usually substantially cylindrical, so that the expansion kit and/or the reaction chamber rests tightly against the wall of the reactor. It is therefore easily possible to control the temperature of the two reaction chambers. Otherwise, the introduced reaction chamber of the expansion kit sits on the bottom of the retrofitted bioreactor.

The volume of the two reaction chambers is particularly preferably in the ratio 1:1, but ratios up to 1:4 are also preferably used, in order to perform a microbial bio-electrosynthesis.

In order to reversibly fix the membrane, the latter is preferably arranged between a seal and a frame, wherein the frame fixes the membrane and the seal to the reaction chamber such that the window is covered.

The way in which the membrane is fixed by means of the frame is in principle known to the person skilled in the art. This can, for example, be bolted or glued or can also be retained by means of a clamping connection.

The size of the window and, thus, the membrane is selected such that the internal resistance is as small as possible. The ratio of the size of the electrodes, which are respectively arranged in the two reaction chambers of the bioreactor, to the size of the window and/or the membrane is therefore expediently in the range of 1:100 to 100:1.

The expansion kit according to the invention is introduced into a reaction chamber of a standard bioreactor according to the prior art and thus divides said bioreactor into two reaction chambers separated by the membrane, so that the retrofitted bioreactor can be used during a microbial electrosynthesis, for example a cathodic hydrogenation, preferably using microbial extracellular electron transfers.

According to a preferred embodiment, a reactor lid is also provided for the expansion kit, said reactor lid sealing the reactor chamber of the expansion kit as well as the original bioreactor, wherein a seal is preferably provided between the reactor chamber of the retrofit kit and the lid.

The reactor lid additionally comprises at least two through-openings for stirrers, electrodes, measuring probes, fumigation or degassing and the like.

The reactor lid comprises standard fastening means in order, for example, to make bolting to the retrofitted bioreactor possible.

The reaction chamber preferably consists of an electrochemically inert material. This is preferably glass, ceramic or a sterilizable plastic such as PTFE or PEEK.

The expansion kit is advantageously suitable for bioreactors made by numerous manufacturers, as said expansion kit is preferably designed for a size of bioreactors which are to be retrofitted of 2 L, a size which is widespread. However, the expansion kit according to the invention is also suitable for other reactor sizes such as, for example, in the range from 0.3 to 5 L and can be designed accordingly.

This expansion kit according to the invention can be used to expand bioreactors made by various manufacturers in such a way that comparable microbial bio-electrosynthesis investigations on a laboratory scale can be advantageously performed in these. It can be used to systematically perform research and development work relating to microbial bio-electrosynthesis under controlled and comparable conditions.

It is also advantageous that recourse can be had to bioreactors which are already available, the associated control technology and peripherals and standard bioreactors can, if required, be converted into bioreactors for bio-electrosynthesis.

It is particularly advantageous that this conversion is reversible, as a result of which expensive double procurements can be avoided.

It is also particularly advantageous that this integration into existing bioreactor systems also makes it possible for the person who is not skilled in the art, in particular the non-electrochemist, to perform such work.

Furthermore, it is very advantageous—which was in no way made possible by previous bioreactor systems according to the prior art—that the reactor which is retrofitted according to the invention on the 2 L scale can be connected, to a large extent, without any problems to the industrial scale, for example, the 400 L scale, and the resulting scalability thereof.

All types of microbial bio-electrosyntheses can be advantageously performed by means of the retrofit kit according to the invention. These include all reduction-oxidation (redox) reactions, i.e. biotransformations involving a change in the redox status of the target molecule, both oxidative (anodic) and reductive (cathodic) processes. These include, for example, the following reactions which can represent a particular added value:
1. Multistage (bio)electrochemical oxidations and reductions as well as the forming of C—C bonds (which cannot be achieved by conventional chemical and enzymatic catalysts),
2. Selective oxidations (avoidance of overoxidation such as when using other oxidizing agents such as atmospheric oxygen),
3. Hydrogenations during "mild" reaction conditions (temperatures of max. 100° C., no $H_2$ atmospheres),
4. Electrochemical fermentations (increasing the yield by the substoichiometric use of electrical energy),
5. Reduction/fixing of $CO_2$ in $C_1$ and $C_{1+n}$ bodies,
6. Use of "electroactive" microorganisms as catalysts with a preferable chemo-, regio-, and stereo-specificity.

In addition, both planktonic processes and biofilm processes can be advantageously performed in bioreactors equipped with the expansion kit.

The subject matter of the invention is, in addition, a bioreactor for performing microbial bio-electrosynthesis comprising an expansion kit. This bioreactor has the features described in the case of the bioreactors to be retrofitted.

Within the framework of the invention, the term "bioreactor" denotes a bioreactor on a technical scale, which is characterized at least by minimal technical equipment and which makes it possible to perform a microbial bio-electrosynthesis.

The minimal technical equipment preferably includes process control preferably of the temperature control, stirrer speed, type and quantity of fumigation as well as pH parameters, and the installation of anode and cathode for controlling the bio-electrosynthesis by means of a potentiostat and/or a direct voltage or direct current source.

Good mixing can therefore take place in the two chambers provided by the expansion kit, in order to avoid the otherwise inevitably occurring gradients in the reaction space (temperature and concentration gradients, etc). These would inevitably lead to productivity losses.

When the expansion kit is used, the two chambers separated by a membrane both fulfil the criteria of a bioreactor on a technical scale.

This also applies correspondingly to the expansion kit alone.

In addition, it must preferably be possible to carry out sterilization at a temperature of at least 121° C.

Advantageous further developments of the invention are indicated in the subordinate claims and described in the specification.

DRAWINGS

Figure 2:
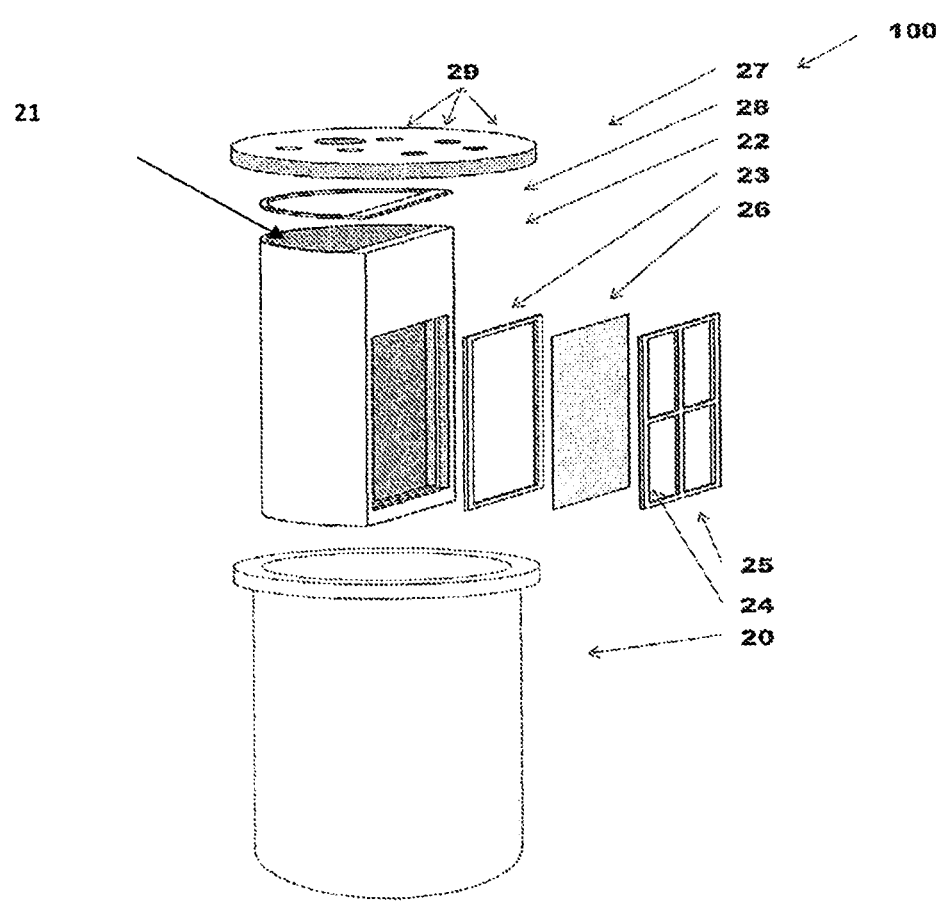

The invention will be explained in greater detail below with reference to drawings and the following description, wherein:

FIG. 1 shows a microbial electrosynthesis by using the example of a cathodic hydrogenation, using microbial extracellular electron transfers according to the prior art in a schematic view, and FIG. 2 shows an expansion kit for bioreactors for performing bio-electrosynthesis in an exploded view.

A microbial electrosynthesis according to the prior art is shown, by way of example, by means of FIG. 1. This involves a cathodic hydrogenation, using a microbial extracellular electron transfer. An anode 13 and a cathode 14 are respectively arranged in two reaction chambers 11, 12 which are separated from each other by a membrane 10, which are connected to a voltage source 15, wherein the cathode 14 is provided with a biofilm 16 of a bio-electrocatalytically active micro-organism. A substrate X is selectively reduced on the cathode 14 to the product $XH_2$, while $H_2O$ is oxidized on the anode 13 to provide $H^+$ and electrons. The corresponding ion transfer 17 takes place through the membrane 10. The product obtained $XH_2$ is conducted away from the reaction chamber 12, while substrate X is fed into it.

Above all, the chemo-, regio- and stereo-specificity of the bio-electrosynthesis is very important for biotechnologically interesting concepts. In this case, the reaction substrate and/or the biofilm is not used as a growth substrate for the biofilm, but a separate growth substrate ensures that the biofilm has stable stationary properties. Similarly, anodic concepts, i.e. for microbial electro-oxidation, can also be developed.

FIG. 2 shows an expansion kit 100 according to the invention for bioreactors 20 used for performing microbial bio-electrosynthesis 20. The expansion kit 100 comprises a reactor chamber 21 which has a cross-section in the form of a circular segment. A rectangular window 23 which can be sealed with a membrane 24 is arranged on the resulting flat sidewall 22 of the reactor chamber 21. To this end, the membrane 24 is fixed with a frame 25 to the reactor chamber 21, wherein a seal 26 is additionally arranged between the membrane 24 and the reactor chamber 21. The reaction chamber 21 is introduced into a reactor 20 which is to be expanded and the reactor 20 is then sealed by means of a lid 27 which is part of the expansion kit 100, wherein a seal 28 is arranged between the reactor chamber 20 and the lid 27. Various through-openings 29 which are intended for electrodes, stirrers, measuring probes, fumigation, degassing and the like are provided in the lid 27.

LIST OF REFERENCE NUMERALS

Membrane 10
Reaction chamber 11, 12
Anode 13
Cathode 14
Voltage source 15
Biofilm 16
Ion transfer 17
Substrate X
Product $XH_2$
Expansion kit 100
Bioreactor 20
Reactor chamber 21
Flat sidewall 22
Rectangular window 23
Membrane 24
Frame 25
Seal 26
Lid 27
Seal 28
Through-opening 29

The invention claimed is:

1. An expansion kit for reversible introduction into a bioreactor for dividing the bioreactor into two separate reaction chambers and for performing microbial bio-electrosynthesis, wherein the expansion kit comprises a reaction chamber which is open at a top and which has a window in a sidewall, said window having a membrane disposed therein, characterized in that the expansion kit is formed such that, when the expansion kit has been introduced into the bioreactor: the reaction chamber of the expansion kit and a reaction chamber of the bioreactor are adjacent to each other on opposite sides of the sidewall and are connected to each other by the membrane disposed in the window of the sidewall, the expansion kit having a reactor lid that covers the open portions of both reaction chambers, the sidewall being coupled to and extending from the reactor lid such that the sidewall is substantially perpendicular to the reactor lid, the reactor lid having at least two through-openings into which electrodes are introduced in such a way that each of the electrodes projects into a separate one of the reaction chambers separated by the membrane and each of the electrodes functions as an anode or cathode.

2. The expansion kit according to claim 1, characterized in that the membrane is ion-selective.

3. The expansion kit according to claim 1, characterized in that the membrane is fixed by a frame to the reaction chamber of the expansion kit.

4. The expansion kit according to claim 1, characterized in that the reaction chamber of the expansion kit comprises a cross-section in the form of a circular segment, wherein the window is configured in the area of a chord of the circular segment.

5. The expansion kit according to claim 1, characterized in that the reaction chamber of the expansion kit comprises a rounded or angular indentation which is provided with a window, at the lowest point of the indentation.

6. The expansion kit according to claim 1, characterized in that the reaction chamber of the expansion kit comprises an electrochemically inert material.

\* \* \* \* \*